(12) United States Patent
Uemura et al.

(10) Patent No.: US 8,034,616 B2
(45) Date of Patent: Oct. 11, 2011

(54) METHOD AND APPARATUS FOR CULTIVATING MULTIPOTENT STEM CELLS

(75) Inventors: Masaru Uemura, Hyogo (JP); Rui Yuge, Hiroshima (JP)

(73) Assignees: Mitsubishi Heavy Industries, Ltd., Tokyo (JP); Rul Yuge, Hiroshima (JP)

( * ) Notice: Subject to any disclaimer, the term of this patent is extended or adjusted under 35 U.S.C. 154(b) by 1164 days.

(21) Appl. No.: 10/540,522

(22) PCT Filed: Dec. 27, 2002

(86) PCT No.: PCT/JP02/13774
§ 371 (c)(1),
(2), (4) Date: Dec. 20, 2007

(87) PCT Pub. No.: WO2004/061092
PCT Pub. Date: Jul. 22, 2004

(65) Prior Publication Data
US 2008/0108136 A1    May 8, 2008

(51) Int. Cl.
*C12N 5/00* (2006.01)
(52) U.S. Cl. ..... 435/377; 435/375; 435/325; 435/283.1; 435/289.1; 435/303.1
(58) Field of Classification Search .................. None
See application file for complete search history.

(56) References Cited

U.S. PATENT DOCUMENTS 5,496,722 A * 3/1996 Goodwin et al. ............. 435/371
5,851,984 A * 12/1998 Matthews et al. ............. 514/2
2003/0041800 A1   3/2003 Uemura et al.

FOREIGN PATENT DOCUMENTS

| EP | 1 249 519 | 10/2002 |
| JP | 7-89798 | 10/1995 |
| JP | 7-89798 B2 | 10/1995 |
| JP | 2002-45173 | 2/2002 |
| WO | WO 95/33821 | 12/1995 |
| WO | 01/29206 A1 | 4/2001 |

OTHER PUBLICATIONS

"Completion of Quasi gravity-less experimental facility (3-D Clinostat)", Daikuken News vol. 44 No. 3, (2000), p. 2.
Sinsuke Kido et al., "Roles of fos family genes in mechanical stress-induced osteogenesis", 23th Annual Meeting of the Molecular Biology Society of Japan Programme & Summaries (2000), W1E-7 p. 261.
Plett, Arthur P. et al.; "Proliferation of Human Hematopoietic Bone Marrow Cells in Simulated Microgravity", In Vitro Cell. Dev. Biol., Feb. 2001 , vol. 37, pp. 73-78.
Japanese Office Action dated Apr. 14, 2010, issued in corresponding Japanese Patent Application No. 2001-197182.

(Continued)

*Primary Examiner* — Lora E Barnhart Driscoll
(74) *Attorney, Agent, or Firm* — Westerman, Hattori, Daniels & Adrian, LLP

(57) ABSTRACT

In a method of cultivating multipotent stem cells, the multipotent stem cells are cultivated while suppressing differentiation of the multipotent stem cells sealed in a first cultivating container. Then, the cultivated multipotent stem cells are cultivated while applying a force to the cultivated multipotent stem cells sealed in a second cultivating container to promote the differentiation of the cultivated multipotent stem cells.

12 Claims, 4 Drawing Sheets

OTHER PUBLICATIONS

Davis, Thomas A. et al.; " Effect of spaceflight on human stem cell hematopoiesis: suppression of erythropoiesis and myelopoiesis"; Journal of Leukocyte Biology, 1996, vol. 60, pp. 69-76.

Jeanne E. Becker et al., "Three-Dimensional Growth and Differentiation of Ovarian Tumor Cell Line in High Aspect Rotating-Wall Vessel: Morphologic and Embryologic Considerations", Journal of Cellular Biochemistry, vol. 51, 1993, pp. 283-289.

Supplementary European Search Report of PCT/JP2004/013774 mailed on Apr. 6, 2006.

* cited by examiner

METHOD AND APPARATUS FOR CULTIVATING MULTIPOTENT STEM CELLS

TECHNICAL FIELD

The present invention relates to a method and apparatus of cultivating indifferent multipotent stem cells. In particular, the present invention relates to a method and apparatus of cultivating an indifferent multipotent stem cells while controlling a differentiation.

BACKGROUND ART

Now, in a regeneration medicine, the consideration of a technique for recovering and regenerating a targeted tissue and organ by using a stem cell transplantation has been advanced. A multipotent stem cell has differentiation potency to differentiate into various mature cells, together with the self-replicating ability to repeat self-multiplication and passage. It is considered that the tissue and organ can be recovered and regenerated by cultivating the multipotent stem cells extracted from a living body, carrying out a differentiation induction and returning into the living body again.

However, now, the subsequent survival rate of transplanted stem cells is low. Although the transplanted stem cells can exist inside the living body, it does not still exhibit an original function of the stem cell. Moreover, since the stem cells change differentiation directions easily depending on an environmental factor, it is impossible to deny a possibility that the transplanted stem cells are not differentiated into the targeted tissue and organ.

In order to establish a stem cell transplanting technique, it is necessary to establish a technique for cultivating multipotent stem cells. At first, it is necessary to establish a technique for cultivating the multipotent stem cells in an indifferentiation state. In addition, it is necessary to establish a technique for transplanting the multipotent stem cells in a proper differentiation process while increasing the subsequent survival rate and also carrying out a proper differentiation induction on the multipotent stem cells in advance.

Conventionally, as the transplanting technique of the stem cells and the differentiation inducing technique, a technique for cultivating the stem cells in a medium containing medical substances serving as a multiplying factor and a differentiating factor is known. Also, a technique for cultivating the stem cells by mixing with different cells is known. However, both of them do not reach a practical use stage. Moreover, an animal plant breeding apparatus for breeding an animal and a plant while rotating a container so as to receive gravitation from many directions is disclosed in Japanese patent Examined application (JP-B-Heisei 7-89798).

DISCLOSURE OF INVENTION

It is therefore an object of the present invention to provide a method and apparatus of cultivating multipotent stem cells that can properly control multiplication and differentiation of the multipotent stem cells.

In an aspect of the present invention, a method of cultivating multipotent stem cells is achieved by (a) cultivating the multipotent stem cells while suppressing differentiation of the multipotent stem cells sealed in a first cultivating container, and (b) cultivating the cultivated multipotent stem cells while applying a force to the cultivated multipotent stem cells sealed in a second cultivating container and inducing the differentiation of the cultivated multipotent stem cells.

The (a) cultivating step may include dispersing the direction of application of gravitation to said multipotent stem cells three-dimensionally to suppress the differentiation. The (a) cultivating step may include carrying out an n-axis rotation (n is an integer of 2 or more) on the multipotent stem cells to disperse the direction of the gravitation three-dimensionally. The n is 2, and it is preferable that one axis is the direction of the gravitation, and the other axis is orthogonal to the direction of the gravitation.

Also, at the (b) cultivating step, the direction of the force is preferably different from the direction of the gravitation. Also, the force is preferably greater than the magnitude of the gravitation. The force may be the resultant force of the gravitation and centrifugal force.

Also, in the second cultivating container, a differentiation inducing agent may be mixed in the medium.

The (a) cultivating step and the (b) cultivating step are preferably carried out in the same apparatus, and the first cultivating container and the second cultivating container are preferably same.

Also, in another aspect of the present invention, a cultivating apparatus includes an inner frame to which a cultivating container accommodating multipotent stem cells is attached; an outer frame configured to rotatably support the inner frame; a first motor configured to rotate the inner frame around a first rotation axis; a supporting section configured to rotatably support the outer frame; and a second motor configured to rotating the outer frame around a second rotation axis.

It is preferable that the second rotation axis is in the direction of the gravitation, and the first rotation axis is in the direction orthogonal to the second rotation axis.

Preferably, the second motor can be rotated independently of the first motor, and the inner frame can be fixed to a predetermined rotation position.

The cultivating container may be attached to the inner frame in the vicinity of the crossing point between the first rotation axis and the second rotation axis. Also, when the multipotent stem cells is cultivated while the differentiation of the multipotent stem cells is suppressed, the cultivating container may be attached to the inner frame in the vicinity of the crossing point between the first rotation axis and the second rotation axis, and when the differentiation of the multipotent stem cells are induced, the cultivating container may be attached to the end portion of the inner frame.

The cultivating container may be attached to the edge of the inner frame.

Also, another aspect of the present invention, a cultivating system of multipotent stem cells includes a first section for cultivating the multipotent stem cells while suppressing differentiation of the multipotent stem cells sealed in a first cultivating container; and a second section for cultivating the multipotent stem cells while applying a force to the cultivated multipotent stem cells sealed in a second cultivating container to promote the differentiation of the multipotent stem cells.

The first section disperses the direction of the gravitation three-dimensionally to suppress the differentiation, and specifically, carries out an n-axis rotation (n is an integer of 2 or more) on the multipotent stem cells to disperse the direction of the gravitation three-dimensionally.

Also, it is preferable that the n is 2, and one axis is the direction of the gravitation, and the other axis is orthogonal to the direction of the gravitation.

Also, it is preferable that the direction of the force is different from the direction of the gravitation and is greater than the magnitude of the gravitation. The force may be the resultant force of the gravitation and centrifugal force. Preferably, the first cultivating container and the second cultivating container are same.

BEST MODE FOR CARRYING OUT THE INVENTION

The present invention relates to U.S. application Ser. Nos. 10/119,895, 10/233,506 and 10/233,566. Those disclosures are incorporated herein by reference.

The cultivating method of the multipotent stem cells according to the present invention will be described below in detail with reference to the attached drawings.

Figure 1:
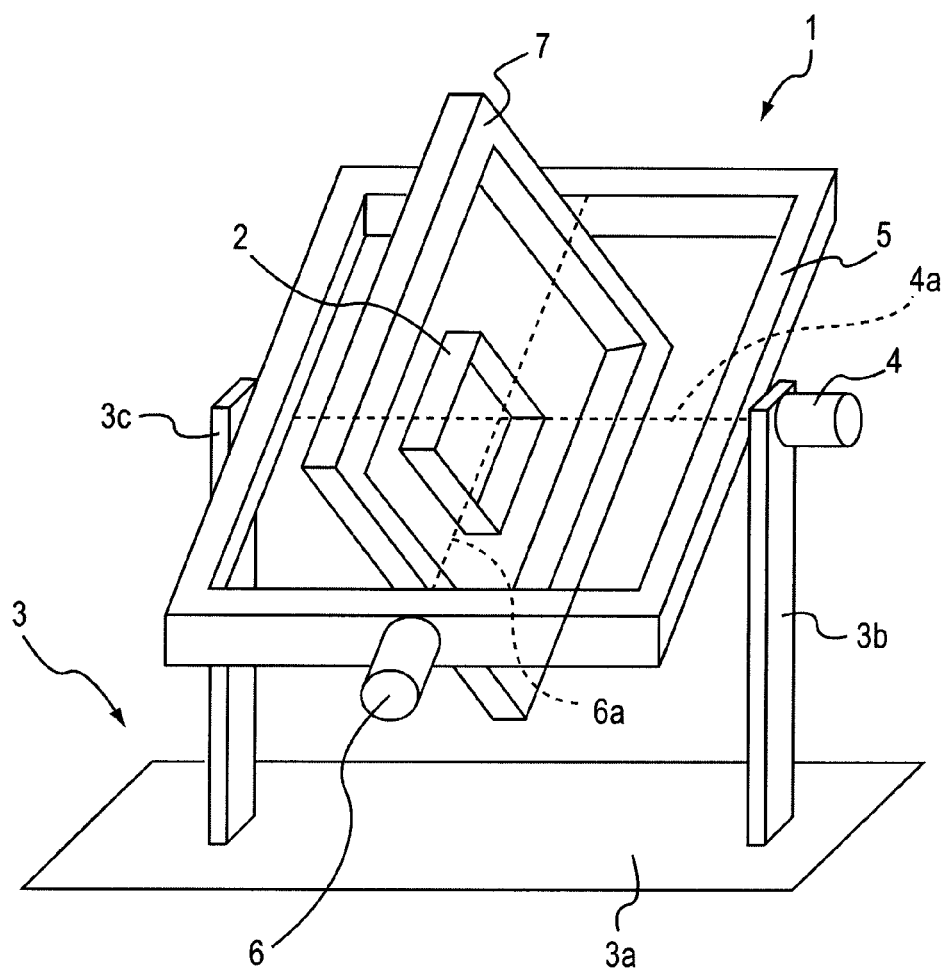
FIG. 1 shows a gravitation dispersing type cultivating apparatus 1 used in a method of cultivating multipotent stem cells according to a first embodiment of the present invention.

At first, in the cultivating method of the multipotent stem cells according to the first embodiment of the present invention, the multipotent stem cells are extracted from a living body. For example, in case of the multipotent stem cells of a rat, bone marrow cells are extracted from a rat femur. The extracted bone marrow cells are suspended in a medium containing a cow fetus serum. The medium in which the bone marrow cells are suspended is separated into a fat component and cell sediment by a centrifugal separating method. The obtained cell sediment is separated into a low density fraction and a high density fraction by using a density gradient centrifugal method. The multipotent stem cells are separated from the low density fraction by a flow cytometry. Subsequently, the extracted multipotent stem cells are cultivated by a gravitation dispersing type cultivating apparatus 1 shown in FIG. 1, while the two-axis rotation is carried out.

The gravitation dispersing type cultivating apparatus 1 includes a cultivating container 2, a main body 3, a motor 4, an outer frame 5, a motor 6 and an inner frame 7. The multipotent stem cells and the medium are sealed in the cultivating container 2. The main body 3 has a base 3a and legs 3b and 3c. The legs 3b and 3c extend upwardly from the base 3a and rotatably support the outer frame 5. The motor 4 connected to the outer frame 5 is provided on the leg 3b. The outer frame 5 is rotated around a rotation axis 4a by the motor 4. The inner frame 7 is rotatably supported by the outer frame 5, and the motor 6 connected to the inner frame 7 is provided on the outer frame 5. The inner frame 7 is rotated around a rotation axis 6a by the motor 6. The rotation axis 6a is substantially orthogonal to the rotation axis 4a. The inner frame 7 can fixedly support the cultivating container 2. The cultivating container 2 is provided inside the inner frame 7 in the vicinity of a crossing point between the rotation axis 4a and the rotation axis 6a. In this way, the cultivating container 2 is rotated as a unit with the inner frame 7. Thus, when the outer frame 5 and the inner frame 7 are respectively rotated, the cultivating container 2 is rotated around the two axes.

Figure 2:
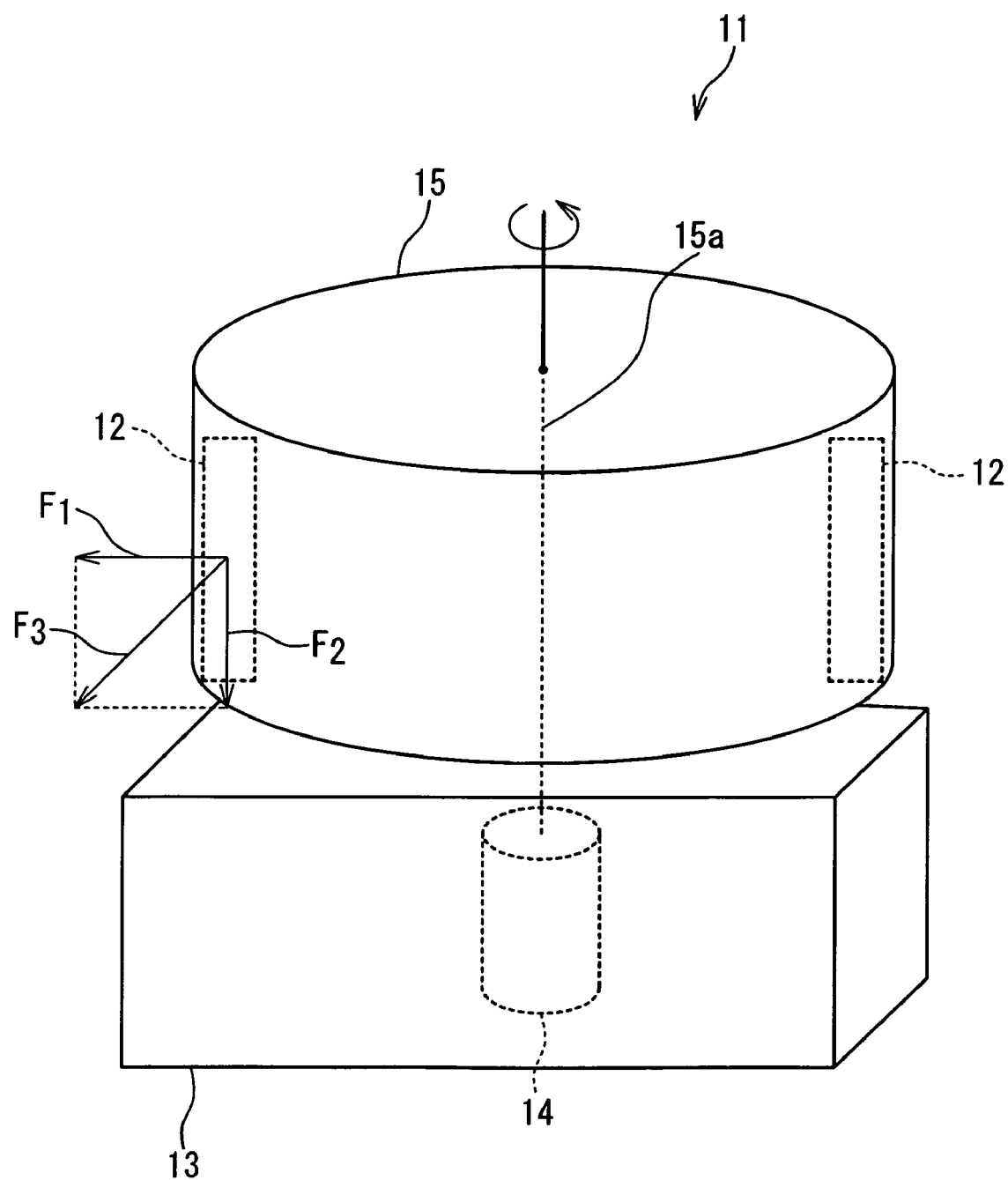
FIG. 2 shows an excessively weighted centrifugal cultivating apparatus 11 used in the method of cultivating the multipotent stem cells according to the first embodiment of the present invention.

When the multipotent stem cells are cultivated while being rotated about the two-axis rotation, the direction of the gravitation applied to the multipotent stem cells is three-dimensionally dispersed, and the multipotent stem cells are multiplied in the sate that the differentiation is suppressed. After the sufficient multiplication, the multipotent stem cells are cultivated by the excessively weighted centrifugal cultivating apparatus 11 shown in FIG. 2.

The excessively weighted centrifugal cultivating apparatus 11 includes a cultivating container 12, a main body 13, a motor 14 and a rotor 15. The medium and the multipotent stem cells cultivated by the gravitation dispersing type cultivating apparatus 1 are sealed in the cultivating container 12. The medium sealed in the cultivating container 12 contains various factors for inducing a desirable differentiation. For example, when the differentiation to a bone and a cartilage should be induced, dexamethasone and TGF-β are mixed into the medium as the differentiation inducing material. The motor 14 is provided for the main body 13 to rotate the rotor 15 around a rotation axis 15a. The rotation axis 15a is substantially parallel to the gravitation direction. The cultivating container 12 is fixed to the rotor 15.

When the rotor 15 is rotated, the centrifugal force is applied to the cultivating container 12. Consequently, a centrifugal force $F_1$ is applied to the multipotent stem cells sealed in the cultivating container 12 in a horizontal direction perpendicular to the gravitation direction. The magnitude of the centrifugal force $F_1$ is greater than the gravitation. Thus, a resultant force $F_3$ of the centrifugal force $F_1$ and a gravitation $F_2$ is applied to the multipotent stem cells sealed in the cultivating container 12. The resultant force $F_3$ is oriented towards a constant direction with respect to the multipotent stem cells and is greater than the gravitation. At this time, since the rotation axis 15a is substantially parallel to the gravitation direction, the relative direction and magnitude of the resultant force $F_3$ with respect to the multipotent stem cells are kept approximately constant. This is desired to promote the differentiation. Also, the cell cultivation surface of the cultivating container 12 is preferably placed vertically to the resultant force $F_3$.

When the multipotent stem cells are cultivated in the state that the relative direction is constant and the force greater than the gravitation is applied, the differentiation of the multipotent stem cells are promoted. The multipotent stem cells are differentiated up to a desirable state and grown to the differentiation induction cells. The differentiation induction cells are used in living body cell transplantation.

In the first embodiment, the multipotent stem cells are cultivated while being rotated around the two-axis rotation. As a result, while the differentiation of the multipotent stem cells are suppressed, the multipotent stem cells can be cultivated. Moreover, after the multipotent stem cells are sufficiently cultivated, the multipotent stem cells are cultivated in the state that the force greater than the gravitation is applied in the constant direction. Thus, the differentiation of the multipotent stem cells is promoted. In this way, in the first embodiment, the multiplication and differentiation of the multipotent stem cells can be properly controlled.

It should be noted that in this embodiment, when the multipotent stem cells are cultivated while the differentiation is suppressed, the two-axis rotation is carried out on the multipotent stem cells. However, the multipotent stem cells may be cultivated while being rotated around the multiple axes more than the two axes. Even if the multipotent stem cells are cultivated under the multiple-axis rotation, the gravitation applied to the multipotent stem cells is three-dimensionally dispersed, like the two-axis rotation. The multipotent stem cells are multiplied in the state that the differentiation is suppressed.

A method of cultivating the multipotent stem cells according to the second embodiment of the present invention will be described below. The method of cultivating the multipotent stem cells according to the second embodiment uses a cultivating apparatus 21 shown in FIG. 3, instead of the gravitation dispersing type cultivating apparatus 1 of FIG. 1 and the excessively weighted centrifugal cultivating apparatus 11 of FIG. 2.

The cultivating apparatus 21 includes a cultivating container 22, a main body 23, a stem 24, motor 25, an outer frame 26, a motor 27 and an inner frame 28. The multipotent stem cells and the medium are sealed in the cultivating container 22. The motor 25 is provided for the main body 23. From the main body 23, the support pillar 24 extends upwardly and then extends horizontally. Thus, the motor 27 and the support pillar 24 rotatably support the outer frame 26. The motor 25 rotates the outer frame 26 around a rotation axis 25*a*. The rotation axis 25*a* is parallel to the gravitation direction. The outer frame 26 rotatably supports the inner frame 28, and the motor 27 is provided for the outer frame 26. The motor 27 rotates the inner frame 28 around a rotation axis 27*a*. The rotation axis 27*a* is substantially orthogonal to the rotation axis 25*a*. The cultivating container 22 is fixedly provided in the inner frame 28 in the vicinity of the crossing point of the rotation axis 27*a* and the rotation axis 25*a*. Also, the inner frame 28 can be stopped and fixed at any rotation position. The cultivating container 22 can be also fixedly provided on the inner side of the inner frame 28. The cultivating apparatus 21 with such a structure has both functions of the gravitation dispersing type cultivating apparatus 1 and the excessively weighted centrifugal cultivating apparatus 11.

In the second embodiment, the multipotent stem cells are cultivated as follows. At first, like the first embodiment, the multipotent stem cells are extracted from the living body. The extracted multipotent stem cells are sealed into the cultivating container 22 together with the medium. The cultivating container 22 is fixedly set in the vicinity of the crossing point of the rotation axis 27*a* and the rotation axis 25*a*, similarly to FIG. 1.

Next, while the two-axis rotation is carried out on the cultivating container 22, the multipotent stem cells are cultivated. That is, in the state that the motor 25 rotates the outer frame 26 and that the motor 27 rotates the inner frame 28, the multipotent stem cells are cultivated inside the cultivating container 22. When the motor 25 rotates the outer frame 26 and the motor 27 rotates the inner frame 28, the two-axis rotation is carried out on the cultivating container 22. When the two-axis rotation is carried out on the cultivating container 22, the gravitation applied to the multipotent stem cells are dispersed three-dimensionally, and the multipotent stem cells are multiplied in the state that the differentiation is suppressed.

Figure 3:
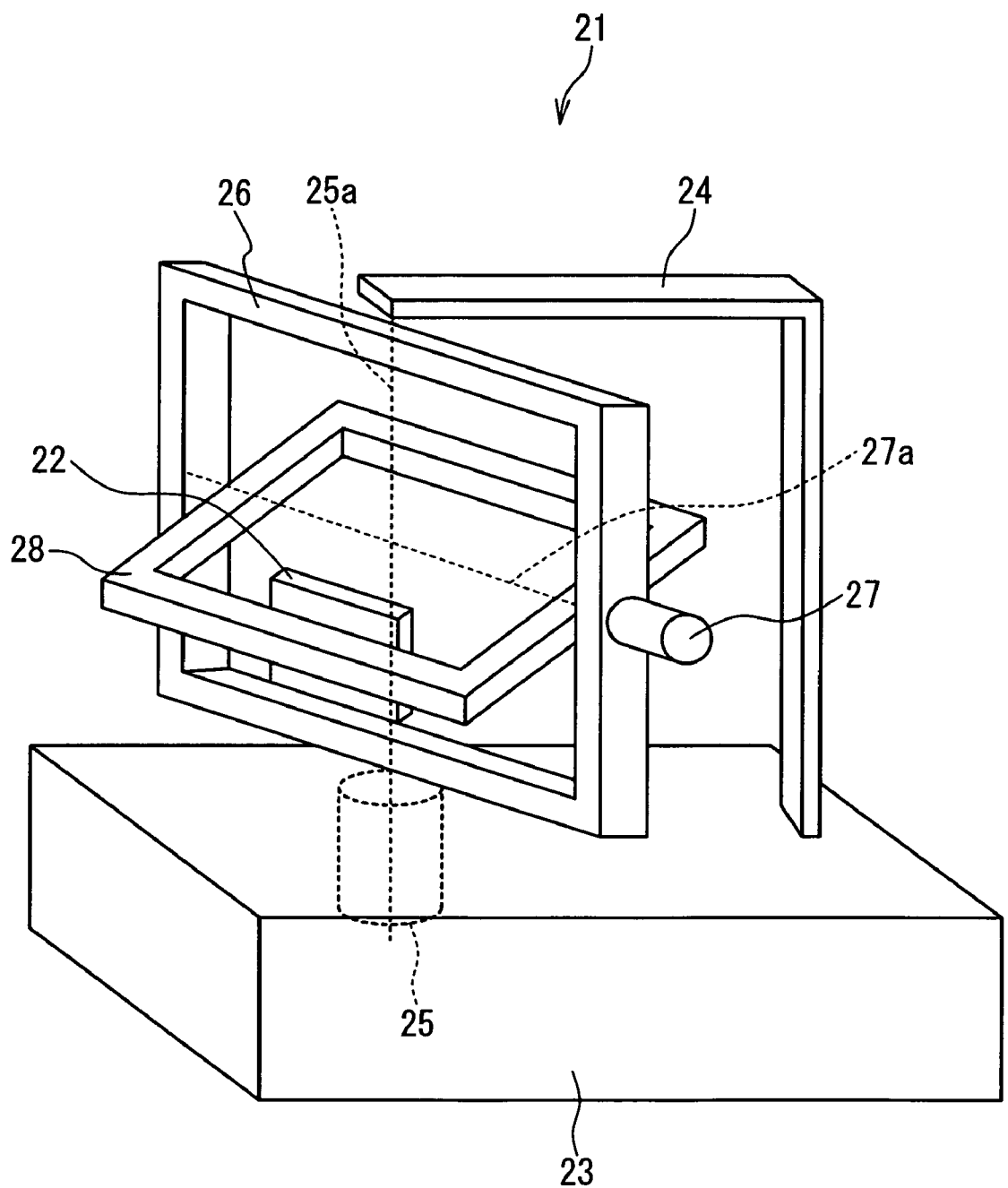
FIG. 3 shows a cultivating apparatus used in a method of cultivating the multipotent stem cells according to a second embodiment of the present invention.

After the sufficient multiplication of the multipotent stem cells, the medium sealed in the cultivating container 22 is replaced with the medium containing various differentiation factors that induce desirable differentiation. Subsequently, as shown in FIG. 3, the inner frame 28 is fixed to a predetermined position, and the cultivating container 22 is also fixedly attached inside the inner frame 28.

Figure 4:
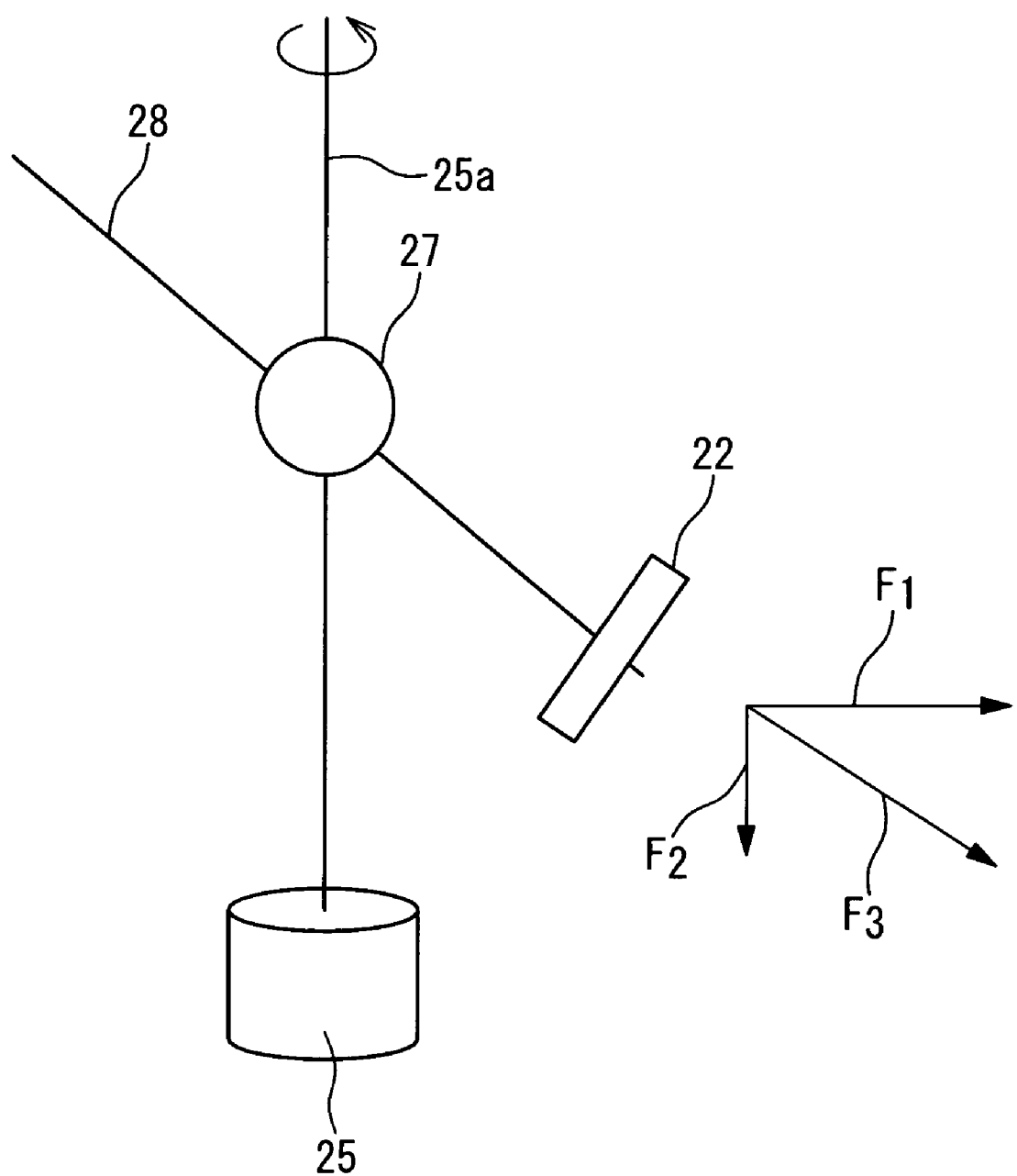
FIG. 4 is a diagram showing an operation of the cultivating apparatus used in the second embodiment.

Next, the multipotent stem cells are cultivated in the state that the force greater than the gravitation is oriented towards a constant direction with respect to the multipotent stem cells and is applied to the multipotent stem cells. In detail, as shown in FIG. 4, the cultivation of the multipotent stem cells are carried out in the state that the outer frame 26 is rotated around the rotation axis 25*a* and that the inner frame 28 is fixed to have a constant angle with respect to the outer frame 26. At this time, the motor 27 does not rotate the inner frame 28. Thus, the one-axis rotation is carried out on the cultivating container 22, and the gravitation $F_2$ together with the centrifugal force $F_1$ is applied to the cultivating container 22. The resultant force $F_3$ of the centrifugal force $F_1$ and the gravitation $F_2$ is applied to the multipotent stem cells sealed in the cultivating container 22. The resultant force $F_3$ is oriented towards the constant direction with respect to the multipotent stem cells and is greater than the gravitation.

As mentioned above, when the multipotent stem cells are cultivated in the state that the force greater than the gravitation is applied to the constant direction, the differentiation of the multipotent stem cells are promoted. The multipotent stem cells are differentiated up to a desirable state and grown to the differentiation induction cells. The differentiation induction cells are used in the living body cell transplantation.

Also, in the second embodiment, similarly to the first embodiment, the multiplication and differentiation of the multipotent stem cells are properly controlled. Moreover, the second embodiment is preferable in the point that the units necessary for the cultivation are reduced compared with the first embodiment.

A method of cultivating the multipotent stem cells according to the third embodiment of the present invention will be described below. The cultivating method of the multipotent stem cells according to the third embodiment uses the cultivating apparatus 21 shown in FIG. 3.

In the third embodiment, the multipotent stem cells are cultivated as follows. At first, like the first embodiment, the multipotent stem cells are extracted from the living body. The extracted multipotent stem cells together with the medium are sealed into the cultivating container 22. The cultivating container 22 is fixedly attached to the inner side of the inner frame 28, as shown in FIG. 3.

Next, while the two-axis rotation is carried out on the cultivating container 22, the multipotent stem cells are cultivated. That is, the multipotent stem cells are cultivated in the cultivating container 22 in the state that the motor 25 rotates the outer frame 26 and that the motor 27 rotates the inner frame 28. When the motor 25 rotates the outer frame 26 and the motor 27 rotates the inner frame 28, the two-axis rotation is carried out on the cultivating container 22. When the two-axis rotation is carried out on the cultivating container 22, the gravitation applied to the multipotent stem cells are dispersed three-dimensionally, and the multipotent stem cells are multiplied in the state that the differentiation is suppressed, like the second embodiment.

After the sufficient multiplication of the multipotent stem cells, the rotations of the inner frame 28 and outer frame 26 are stopped, and the medium sealed in the cultivating container 22 is replaced with the medium containing various differentiation factors that induce the desirable differentiation. Subsequently, as shown in FIG. 4, in the state that the outer frame 26 is rotated around the rotation axis 25*a* and that the inner frame 28 is fixed to have a constant angle with respect to the outer frame 26, the cultivation of the multipotent stem cells is carried out. Consequently, the multipotent stem cells are cultivated in the state that the force greater than the gravitation is oriented towards the constant direction with respect to the multipotent stem cells and is applied to the multipotent stem cells.

In detail, at this time, the motor 27 does not rotate the inner frame 28. Consequently, the one-axis rotation is carried out on the cultivating container 22, and the gravitation $F_2$ together with the centrifugal force $F_1$ is applied to the cultivating container 22. The resultant force $F_3$ of the centrifugal force $F_1$ and the gravitation $F_2$ is applied to the multipotent stem cells sealed in the cultivating container 22. The resultant force $F_3$ is oriented towards the constant direction with respect to the multipotent stem cells and is greater than the gravitation.

According to the present invention, the method and apparatus of cultivating the multipotent stem cells are provided to make it possible to properly control the multiplication and differentiation of the multipotent stem cells.

The invention claimed is:

1. A method of cultivating multipotent stem cells, comprising:
    (a) cultivating multipotent stem cells sealed in a first cultivating container while rotating said multipotent stem cells about at least two orthogonal axes, thereby suppressing differentiation of said multipotent stem cells to obtain cultivated multipotent stem cells; and then
    (b) cultivating said cultivated multipotent stem cells sealed in a second cultivating container while applying at least a centrifugal force by rotating said cultivated multipotent stem cells about one axis, thereby inducing differentiation of said cultivated multipotent stem cells.

2. The method of cultivating multipotent stem cells according to claim 1, wherein in step (b), said cultivated multipotent stem cells are cultured in a medium including a differentiation inducing agent.

3. The method of cultivating multipotent stem cells according to claim 1, wherein said first cultivating container and said second cultivating container are the same container.

4. The method of cultivating multipotent stem cells according to claim 1,
    wherein said at least two orthogonal axes includes a first rotation axis and a second rotation axis,
        wherein said step (a) comprises:
            attaching said first cultivating container, containing said multipotent stem cells, to an inner frame of an apparatus which is rotatably supported by an outer frame of the apparatus;
            rotating said inner frame around the first rotation axis; and
            rotating said outer frame around the second rotation axis, and
    wherein said first cultivating container is attached to said inner frame in a vicinity of a crossing point between said first rotation axis and said second rotation axis.

5. The method of cultivating multipotent stem cells according to claim 4, wherein said step (b) comprises:
    attaching said second cultivating container, containing said cultivated multipotent stem cells, to an end portion of said inner frame;
    rotating said inner frame around said first rotation axis; and
    rotating said outer frame around said second rotation axis.

6. The method of cultivating multipotent stem cells according to claim 1,
    wherein said at least two orthogonal axes includes a first rotation axis and a second rotation axis,
    wherein said step (b) comprises:
        attaching said second cultivating container to an end portion of an inner frame of an apparatus which is rotatably supported by an outer frame of the apparatus;
        rotating said inner frame around a first rotation axis; and
        rotating said outer frame around a second rotation axis.

7. The method of cultivating multipotent stem cells according to claim 1, wherein said first cultivating container and said second cultivating container are different.

8. The method of cultivating multipotent stem cells according to claim 1, wherein said step (a) and said step (b) are carried out in the same apparatus.

9. The method of cultivating multipotent stem cells according to claim 1, wherein said step (a) and said step (b) are carried out in different apparatuses.

10. A cultivating system of multipotent stem cells, comprising:
    first means for cultivating multipotent stem cells while rotating said multipotent stem cells about at least two orthogonal axes; and
    second means for cultivating the cultivated multipotent stem cells while applying at least a centrifugal force by rotating the cultivated multipotent stem cells about one axis,
    wherein said first means and said second means are the same, and
    wherein a cultivating container is attached to an end portion of an inner frame of said first and second means.

11. The cultivating system of multipotent stem cells according to claim 10, wherein said first means and said second means include a single cultivating container.

12. A cultivating system of multipotent stem cells, comprising:
    first means for cultivating multipotent stem cells while rotating said multipotent stem cells about at least two orthogonal axes; and
    second means for cultivating the cultivated multipotent stem cells while applying at least a centrifugal force by rotating the cultivated multipotent stem cells about one axis,
    wherein said first means and said second means are different.

* * * * *